United States Patent [19]

Solomon

[11] 4,327,289

[45] Apr. 27, 1982

[54] IONIZATION DETECTOR CALIBRATION

[76] Inventor: Elias E. Solomon, 20 Christina Ct., Duxbury, Mass. 02332

[21] Appl. No.: 972,661

[22] Filed: Dec. 26, 1978

[51] Int. Cl.³ .................... G01D 18/00; H01J 47/02
[52] U.S. Cl. .................................. 250/252; 250/381
[58] Field of Search ............... 340/629; 250/381, 389, 250/252, 382, 384, 385

[56] References Cited

U.S. PATENT DOCUMENTS

| | | | |
|---|---|---|---|
| 3,710,110 | 1/1973 | Lampart et al. | 250/381 |
| 4,021,671 | 5/1977 | Solomon | 250/381 |
| 4,027,165 | 5/1977 | Jacobs | 340/629 |
| 4,081,684 | 3/1978 | Wieder | 250/252 |
| 4,189,644 | 2/1980 | Schubert et al. | 250/381 |
| 4,194,191 | 3/1980 | Salem | 250/381 |

FOREIGN PATENT DOCUMENTS

| | | | |
|---|---|---|---|
| 2744831 | 6/1978 | Fed. Rep. of Germany | 250/381 |
| 2815231 | 11/1978 | Fed. Rep. of Germany | 250/384 |

Primary Examiner—Alfred E. Smith
Assistant Examiner—Carolyn E. Fields
Attorney, Agent, or Firm—Wolf, Greenfield & Sacks

[57] ABSTRACT

A technique for calibrating an ionization detector by simulating the presence of particles of combustion. In one embodiment a test probe is employed extending into the chamber. The probe may be partially conductive and partially non-conductive and be either rotatable or able to be withdrawn or partially withdrawn to vary ionization current. In another embodiment the source may be moveable to alter the ionization current. In still another embodiment there is provided the temporary distortion of one electrode to change the geometry of the chamber to thereby effect ionization.

4 Claims, 9 Drawing Figures

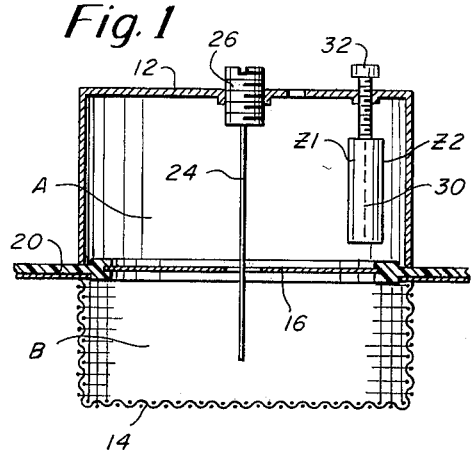
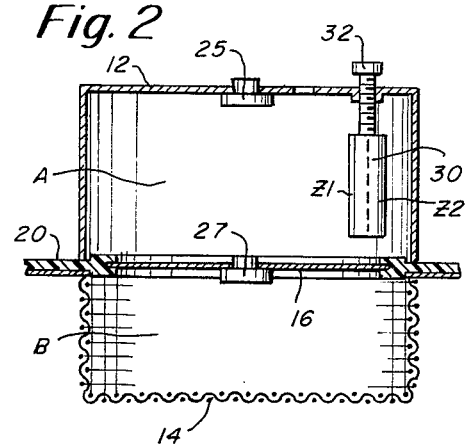
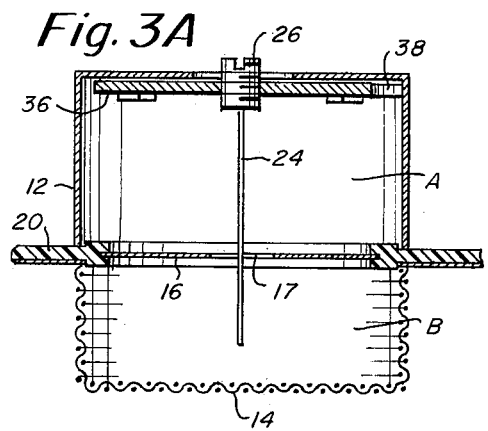
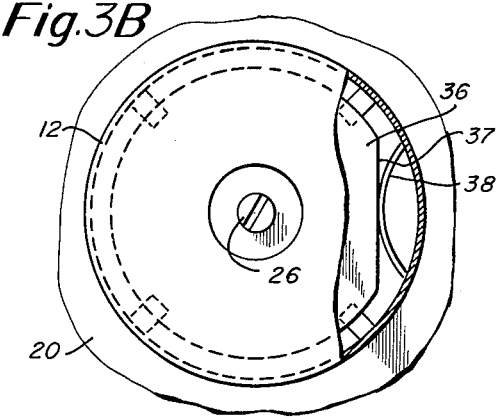
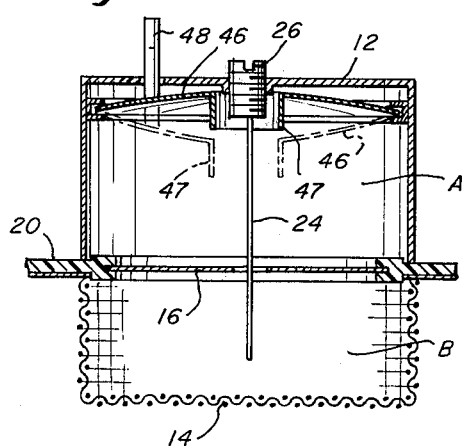
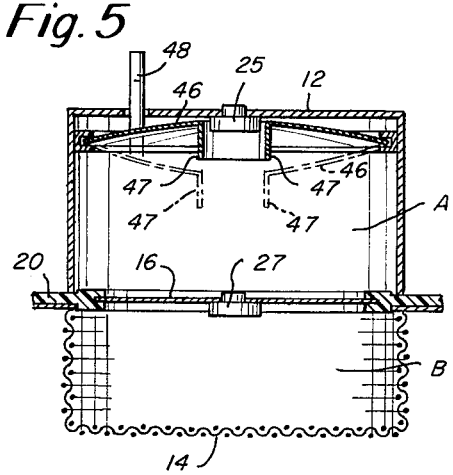

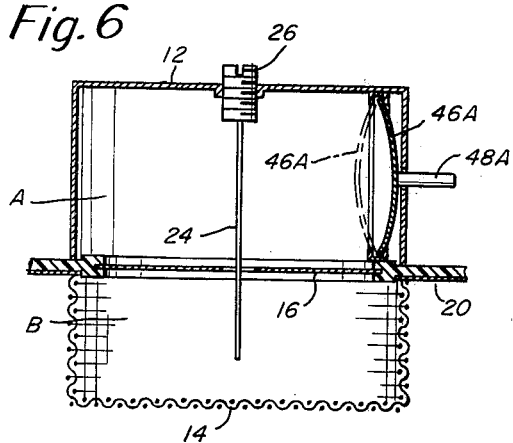
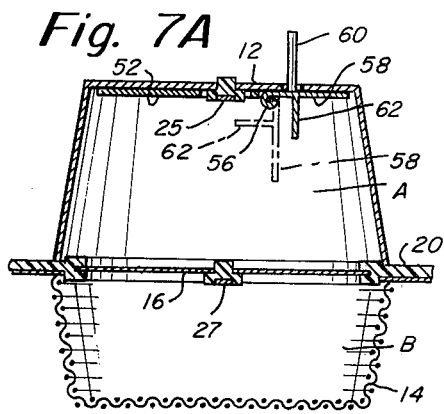
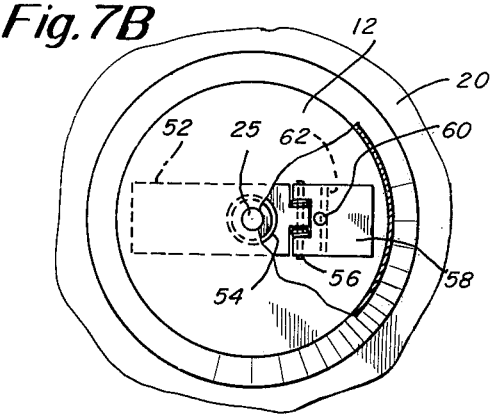

IONIZATION DETECTOR CALIBRATION

BACKGROUND AND SUMMARY OF THE INVENTION

The present invention relates in general to ionization detectors, and more particularly to a calibration apparatus for testing ionization detectors. In accordance with the invention there is provided a predictable technique for simulating the presence of particles of combustion in the chamber or chambers of an ionization detector. The ionization detectors may be of the type shown in U.S. Pat. Nos. 4,021,671 and 4,121,717 and my co-pending application Ser. No. 959,102, filed Nov. 9, 1978.

U.S. Pat. Nos. 4,021,671 and 4,121,718 show the use of a particle capturing member for altering ionic current flow between the electrodes of an ionization chamber. This member is meant to be adjusted and maintained in some preset position. On the other hand, in accordance with the present invention there is provided a calibration means and method to simulate the presence of particles of combustion within the chamber or chambers of an ionization detector. The calibration means preferably has a rest position and is only temporarily moved to a particle simulating position for test purposes.

To accomplish the calibration in accordance with this invention there is provided means associated with the detector for temporarily altering the ionization current flowing between the electrodes so as to simulate the presence of particles of combustion within the chamber.

One important object of the present invention is thus to provide a calibration means and associated method for simulating the presence of particles of combustion within the chamber or chambers of an ionization detector.

Another object of the present invention is to provide such a means and method capable of providing a predictable simulation of the presence of particles of combustion.

Still another object of the present invention is to provide calibration means and method in accordance with the preceding objects and which can be accomplished quite quickly and easily.

To accomplish the foregoing and other objects of this invention there is provided an ionization detector having a chamber, electrodes associated with the chamber and an ionization source which is preferably a Beta ionization source. In accordance with the invention apparatus is provided for calibrating the detector to simulate the presence of particles of combustion. There are disclosed herein a number of different embodiments for accomplishing this purpose. In accordance with one embodiment probe means are provided extending into the chamber and having a first fixed position wherein the ionization current is unaltered and a second temporary position wherein the ionization current is lower to simulate particles of combustion. In this embodiment the probe may have two zones associated therewith including a conductive zone and a less conductive zone. The probe being rotatable to expose either zone toward the ionization current path. In accordance with another embodiment of the invention means are provided for supporting the ionization source and moving the source support means to move the source temporarily from a rest position to a position laterally from the ionization path. In still another embodiment of the present invention the calibration is provided by employing deflectable means supported within the chamber and having a first fixed position and a second temporary position. The first and second positions define different geometries for the detector chamber wherein the ionization current is altered to simulate particles of combustion by means of this change in chamber geometry. The deflecting means may include a tensioning member and manual actuating means for operating the tensioning member. This member may be located at virtually any position within the chamber to change the geometry (volume) thereof. The deflectable member is also preferably constructed with wings or the like about the source to collimate the radiation emanating into the chamber.

In accordance with the method of the present invention again, this method is practiced in association with a detector having a chamber, electrodes associated with the chamber and a radioactive source disposed at some position within the chamber. The method may also be practiced with a dual chamber arrangement or possibly even a triple chamber arrangement as disclosed in my U.S. Pat. No. 4,121,718. In accordance with the method means are associated with the chamber with said means capable of assuming one of two different positions. In accordance with the method the means may be maintained in a first position representative of a normal operating position for the detector and is movable to a temporary position for simulating the presence of particles of combustion.

BRIEF DESCRIPTION OF THE DRAWINGS

Numerous other objects, features and advantages of the invention should now become apparent upon a reading of the following detailed description taken in conjunction with the accompanying drawings, in which:

FIG. 1 schematically illustrates an ionization detector including two chambers and a single radioactive source along with a probe means for simulating particles of combustion;

FIG. 2 is a schematic diagram similar to the one of FIG. 1 also employing a probe means but including two radioactive sources one associated with each chamber;

FIGS. 3A and 3B show another embodiment of the present invention in the form of an ionization detector of the dual chamber type employing a single radioactive source wherein the simulation of particles of combustion is by means of temporary movement of the source;

FIG. 4 shows another embodiment for a detector in accordance with this invention employing a single radioactive source as in FIG. 1 but employing a deflectable member for altering the ionization current to simulate particles of combustion by virtue of changing the chamber geometry (volume);

FIG. 5 shows an arrangement similar to that depicted in FIG. 4 for a dual chamber construction employing two radioactive sources one associated with each chamber of the detector;

FIG. 6 is a schematic diagram similar to the one depicted in FIGS. 1 and 4 employing a single radioactive source but having the deflectable member on the side of the chamber rather than on the top; and FIGS. 7A and 7B show another embodiment of the present invention in the form of an ionization detector of the dual chamber type employing a single radioactive source and including a hinge member useable to collimate the ionization source.

DETAILED DESCRIPTION

FIG. 1 shows a first embodiment of the present invention illustrated in a somewhat schematic fashion. For a more detailed description of a general two-chamber detector reference is made to U.S. Pat. No. 4,021,671. In the detector, such as the one shown in this prior art patent, the electrodes 12 and 14 have a biasing potential applied thereto for establishing an ionization current in the chambers A and B. It is typical in a dual chamber construction to sense outputs from the center, common, or node electrode 16 also depicted in FIG. 1. In FIG. 1 the electrode 14 may be of mesh construction, so that the chamber B is quite open. On the other hand, the chamber A is substantially closed except for a small hole to atmosphere. A hole is preferably also provided in the area of electrode 16 to permit communication to some extent between chambers A and B. The electrodes 12, 14 and 16, of course, are conductively separated and may be supported from a printed circuit board 20 such as is also shown in the prior U.S. Patent referred to hereinabove. FIG. 1 also shows the radioactive source 24 which may be in the form of a radioisotope pin or rod. This member 24 may also be a wire or ribbon and is supported from an adjusting screw 26 supported from the wall of the top chamber A. An insulating bushing (not shown) may also be associated with the structure coupled between the radioactive source 24 and the electrode 16. This bushing and the arrangement of the source and adjusting member is substantially the same as shown in one embodiment disclosed in my co-pending application, Ser. No. 959,102, filed Nov. 9, 1978.

In accordance with the present invention there is associated with the ionization detector of FIG. 1, a probe 30 having a manual actuating end or handle 32 extending through a wall of the chamber. The probe 30 is preferably provided with two separate conductive zones Z1 and Z2. Zone Z1 may be wholly or at least partially conductive while the other zone Z2 is less conductive than zone Z1 or possibly non-conductive. It is preferred that the probe 30 make electrical contact with the electrode 12. The handle end of the probe may be supported by being screwed into an internally threaded passage through the electrode 12. The probe 30 may be of cylindrical shape with each of the zones Z1 and Z2 surrounding one-half of the cylinder.

Under normal operating conditions the probe 30 is in the position depicted in FIG. 1 with the zone Z1 facing the source 24 and with the probe 30 essentially functioning as a part of the electrode 12. However, if the probe 30 is rotated 180° so that the left conductive zone or non-conductive zone Z2 is presented or faces the ionization path then the ability of the probe to capture ions is reduced. This causes a lowering of the ionic current thus simulating ion capture by combustion products. Once this calibration or testing has occurred then the probe may then be rotated back to the position indicated in FIG. 1.

The simulation of ion capture can also be accomplished if the probe 30 is moved further away from the source 24 so that the probe is less likely to capture ions thus, likewise, reducing the ionic current. This could be accomplished in the embodiments of FIGS. 1 and 2 by moving or sliding the probe sideways or this could also be accomplished by partially or wholly withdrawing the probe from the chamber. Of course, in order to provide adequate withdrawal the probe and chamber construction might have to be slightly different than that depicted in FIGS. 1 and 2.

FIG. 2 shows a construction quite similar to the one shown in FIG. 1 including the electrodes 12, 14 and 16, the printed circuit board 20, chambers A and B, and the probe 30. The probe 30 depicted in FIG. 2 may be substantially identical to the one shown in FIG. 1. The chambers A and B may be, respectively, detection and reference chambers. The primary difference between the two embodiments of FIGS. 1 and 2 is that the embodiment of FIG. 1 uses a single source whereas in FIG. 2 there are shown radioactive sources 25 and 27 one being associated with each of the chambers A and B, respectively. The different modes of operation of the probe are substantially the same in FIG. 2 as previously discussed with reference to FIG. 1.

In the embodiments of FIGS. 1 and 2 it is preferred that the probe return essentially automatically to its normal position as depicted in FIGS. 1 and 2. This can be accomplished quite easily by providing a torsion mechanism or a spring mechanism. Such mechanisms are not specifically disclosed in FIGS. 1 and 2 but are well-known mechanisms that could be associated with the probe to return it to a particular predetermined position.

FIGS. 3A and 3B represent a further embodiment of the present invention which simulates the presence of particles of combustion by temporarily moving the radioactive source relative to the chamber electrodes. In FIGS. 3A and 3B the electrodes are represented by the same reference characters as used previously. This embodiment also shows the adjusting screw 26 and radioactive rod source 24 supported from the adjusting screw 26. In this embodiment the adjusting screw is not supported from the electrode 12 but it is instead supported from a movable plate 36 disposed at the top of the detector and having associated therewith a biasing spring 38. As depicted in FIG. 3B the movable plate 36 has a flat side 37 against which the spring 38 may urge. In the embodiment of FIGS. 3A and 3B the opening 17 for accommodating the source 24 may be larger than in FIGS. 1 and 2 so as to accommodate this lateral movement of the source 24. Also, a manual knob may be secured to the movable plate 36 for moving the plate against the bias of spring 38 to a calibrating position to simulate particles of combustion. The spring 38 then returns the movable plate 36 to a normal position when the knob (not shown) is released.

FIGS. 4 and 5 show still another embodiment of the present invention. The embodiment of FIG. 4 employs a single radioactive source in the form of a rod or pin source 24 supported from the adjusting screw 26 which is in turn threadly supported with the top section of electrode 12. The chamber construction shown in FIG. 4 including chambers A and B may be of substantially cylindrical shape and there is provided at the top thereof a tensioning disc or possibly only a strip 46 supported between the sidewalls of chamber A. A channel member may run about the inner surface of chamber A for accommodating the disc 46. In FIG. 4 the disc is shown in-solid in its upper position and in-dotted in a lower position. The disc 46 may be moved between these positions by means of the plunger 48 extending eternally at one end from the chamber A. The disc 46 normally lies substantially flat against the electrode 12 in the position shown in-solid in FIG. 4. The disc 46 is preferably conductive and may be perforated or actually of any other desirable shape which may depend upon the particular shape of the chamber A. Upon operation of the plunger 48 the disc or strip 46 is tensioned to the position shown in-dotted in FIG. 4. This changes the geometry or volume of the chamber A thus altering the ionization current to simulate particles of combustion within the detection chamber A.

The disc 46 is preferably made of a relatively thin metal that is quite readily deflectable. Without the use of any separate spring mechanism the disc 46 may be in either position as a rest position requiring movement by means of the plunger 48 to move it to its opposite position. If the chamber geometry is such that it is desired to increased the electrode spacing or effective volume, then the normal position may be the position shown in-dotted while the plunger would then be used for calibration and test purposes to move the disc to the position shown in-solid in FIG. 4.

The tensioning disc 46 may also be designed and preferably is designed so that the disc 46 has only one rest position and when it is tensioned to the opposite position and the plunger is released, the disc will automatically return to its original desired position for normal operation.

FIG. 5 shows a construction substantially the same as depicted previously in FIG. 2 including two radioactive sources 25 and 27 associated, respectively, with the chambers A and B. FIG. 5 also shows the tensioning disc 46 which may be of the same type discussed previously with regard to FIG. 4. The tensioning disc 46 in both FIGS. 4 and 5 is, of course, open at its center so that it can clear the radioactive source. Also, in FIGS. 4 and 5 the disc 46 is shown in chamber A. It could also be disposed in chamber B or it can be applied in many other manners.

For example, FIG. 6 shows another dual chamber construction similar to the one depicted in FIG. 4 including the electrodes 12, 14 and 16, printed circuit board 20, adjusting screw 26 and pin radioactive source 24. Instead of the disc being provided at the top of chamber A there is provided a disc 46A having associated therewith a plunger 48A for operating the disc 46A. In the position shown in solid in FIG. 6 the geometry of the chamber and its volume is at a maximum while the plunger 48A may operate the disc 46 to a position shown in dotted on a temporary basis to change the geometry of the chamber and thereby simulate particles of combustion. In FIGS. 4-6, the deflectable member may be, as an alternative to the disc, a section of a disc or a strip.

FIGS. 7A and 7B show a construction substantially the same as previously depicted in FIG. 5 employing a dual chamber arrangement including chambers A and B and also employing two sources 25 and 27. The source 25 is preferably supported from the electrode 12 and may be insulatedly supported therefrom. Similarly, the source 27 may be insulatedly supported from the electrode 16. To provide the calibration in accordance with the present invention there is also provided a strip 52 which may be constructed of either a conductive or non-conductive material. The strip 52 is suitably supported at the top of chamber A and may be supported from the top section of electrode 12. The strip 52 has near its center a hole 54 for accommodating the source 55 and a hinge pin 56 for hinging the movable strip 58 from the fixed strip 52. The movable strip 58 has associated therewith a plunger 60 and a wing member 62. In FIG. 7A the wing member 52 is shown in a vertical position in solid and is also shown in dotted in a horizontal position. The hinge arrangement is preferably spring loaded such as by having a spring associated with the hinge pin 56. This spring biases the hinge member 58 to the position shown in solid in FIG. 7A. This is the permanent position of the hinge member and the position that it assumes when calibration is not occurring. When one wishes to calibrate the device, particles of combustion are simulated by urging the plunger 60 downwardly to temporarily move the entire hinge member 58 to the position shown in dotted in FIG. 7A. In this position the ionization source 25 is collimated. Once the calibration procedure is over then the plunger 60 can be released and the hinge member returns to its initial rest position.

This collimation of the output from the radioactive source is also provided in the embodiment of FIGS. 4 and 5 wherein the disc 46 has wings 47 extending downwardly from the center aperture of the disc 46. This arrangement collimates (attenuates) radiation into the detection chamber in the second temporary position shown in dotted in FIGS. 4 and 5. This attenuation or collimation effectively reduces the ionization current to simulate particles of combustion. Similarly, the movement of the hinge member 58 in FIGS. 7A and 7B also collimates radiation into the chamber in particular in the second temporary position shown in dotted in FIGS. 7A and 7B thus effectively reducing the ionization current to simulate particles of combustion.

Herein the calibration means has been described in association with one of the chambers. However, in association with the invention it may be utilized with the other chamber, such as chamber B in FIGS. 1 and 2.

What is claimed is:

1. For an ionization detector having a chamber, electrodes associated with the chamber and an ionization source, apparatus for calibrating the detector to simulate the presence of particles of combustion comprising, probe means extendable into the chamber and having a first fixed position wherein the ionization current is unalterable, and a second temporary position wherein the ionization current is lowered to simulate particles of combustion, said probe means being constructed with at least two zones including a first zone of an electrically conductive material and a second zone having an electrical conductivity less than that of the first zone.

2. For an ionization detector having a chamber, electrodes associated with the chamber and an ionization source, apparatus for calibrating the detector to simulate the presence of particles of combustion comprising, means associated with the chamber and having a first fixed position wherein the ionization current is unaltered, and a second temporary position wherein the ionization current is lowered to simulate particles of combustion, said particle simulation means including attenuation means and means for pivotally supporting the attenuation means whereby in the first position the attenuation means is disposed laterally of and substantially outside of the ionization path and in the second position is pivotally moved at least partially into the ionization path to attenuate ionization current and thus simulate particles of combustion.

3. For an ionization detector as set forth in claim 2, said attenuation means including a wing member extending in a direction orthogonal to the ionization path in the second position.

4. A method for calibrating an ionization detector for simulating the presence of particles of combustion, the detector having a chamber, electrodes associated with the chamber and an ionization source, the method comprising the steps the attenuation means in a first position for establishing a first ionization current whereby the attenuation means is disposed laterally of and substantially outside of the ionization path and temporarily pivotally moving the attenuation means to a second laterally disposed position at least partially into the ionization path wherein the ionization current is lowered to simulate particles of combustion.

* * * * *

UNITED STATES PATENT OFFICE
CERTIFICATE OF CORRECTION

Patent No. 4,327,289  Dated April 27, 1982

Inventor(s) Elias E. Solomon

It is certified that error appears in the above-identified patent and that said Letters Patent are hereby corrected as shown below:

Claim 4, Column 7, line 2 delete "the", second occurrence, and insert -- of providing an --; after the word "means" insert the following: -- associated with the chamber and means for pivotally supporting the attenuation means, msintaining the attenuation means --.

*Signed and Sealed this*

*Tenth* Day of *August 1982*

[SEAL]

*Attest:*

*Attesting Officer*

GERALD J. MOSSINGHOFF

*Commissioner of Patents and Trademarks*